US007964347B2

(12) United States Patent
Dimitrov (10) Patent No.: US 7,964,347 B2
(45) Date of Patent: Jun. 21, 2011

(54) LABELS FOR ELECTRONIC DETECTION OF INDIVIDUAL MOLECULES AND METHODS FOR THEIR DETECTION

(76) Inventor: Krassen Dimitrov, Indooroopilly (AU)

( * ) Notice: Subject to any disclaimer, the term of this patent is extended or adjusted under 35 U.S.C. 154(b) by 31 days.

(21) Appl. No.: 11/762,003

(22) Filed: Jun. 12, 2007

(65) Prior Publication Data

US 2007/0292877 A1        Dec. 20, 2007

Related U.S. Application Data

(60) Provisional application No. 60/814,377, filed on Jun. 15, 2006.

(51) Int. Cl.
    *C12Q 1/68*        (2006.01)
(52) U.S. Cl. .................. 435/6; 536/24.31; 536/24.32
(58) Field of Classification Search ... 435/6; 536/24.31, 536/24.33
    See application file for complete search history.

(56) References Cited

U.S. PATENT DOCUMENTS

| 5,198,367 | A | 3/1993 | Aizawa et al. |
| 2003/0013091 | A1* | 1/2003 | Dimitrov ........................ 435/6 |
| 2003/0059822 | A1* | 3/2003 | Chan et al. ........................ 435/6 |
| 2005/0258362 | A1 | 11/2005 | Collings |
| 2007/0138384 | A1 | 6/2007 | Keiser |
| 2007/0166708 | A1 | 7/2007 | Dimitrov |

FOREIGN PATENT DOCUMENTS

| WO | WO 98/04740 A1 * | 2/1998 |
| WO | WO 2005036156 A1 * | 4/2005 |
| WO | 2007/076128 A2 | 7/2007 |
| WO | 2007/076129 A2 | 7/2007 |

OTHER PUBLICATIONS

Cass et al., Ferrocene-Mediated Enzyme Electrode for Amperometric Determination of Glucose, Anal. Chem. 1984, pp. 667-671, vol. 56.
Penner et al., Fabrication and Use of Nanometer-Sized Electrodes in Electrochemistry, Science, New Series, Nov. 23, 1990, pp. 1118-1121, vol. 250, No. 4984.
Sanna et al., Rapid Induction of Tumor Necrosis Factor alpha in the cerebrospinal Fluid After Intracerebroventricular Injection of Lipopolysaccharide Revealed by a sensitive Capture Immuno-PCR Assay, Proc. Natl. Acad. Sci. USA, Jan. 1995, pp. 272-275, vol. 92.
Barkema et al., Magnetophoresis of Tagged Polymers, Europhsyics Letters, Jul. 10, 1996, pp. 139-144, vol. 35(2).
Ciszkowska et al., Voltammetry in Solutions of Low Ionic Strength. Electrochemical and Analytical Aspects, Journal of Electroanalytical Chemistry, 1999, pp. 129-143, vol. 466.

Watarai et al., Magnetophoretic Behavior of Single Polystyrene Particles in Aqueous Manganese (II) Chloride, Analytical Sciences Oct. 2001, pp. 1233-1236, vol. 17.
Nakane et al., Evaluation of Nanopores as Candidates for Electronic Analyte Detection, Electrophoresis 2002, pp. 2592-2601, vol. 23.
Nakane et al., Nanopore Sensors for Nucleic Acid Analysis, Institute of Physics Publishing, Journal of Physics: Condensed Matter, Aug. 31, 2003, pp. R1365-R1393, vol. 15.
Drzewinski et al., Pulling Reptating Polymers by One End: Magnetophoresis in the Rubinstein-Duke Model, Physical Review, Dec. 18, 2003, pp. 061801-1-061801-6, vol. 68.
Watarai et al., Magnetophoresis and Electromagnetophoresis of Microparticles in Liquids, Anal Bioanal Chem, Dec. 13, 2004, pp. 1693-1699, vol. 378.
Schiavo et al., Pushing the Limits of Detection with Immuno-PCR, PharmaGenomics, Jan. 2004, pp. 36-45.
Ying et al., A Novel Magnetic Separation Technique: Selective Separation of Ultrafine Particles by Magnetophoresis, Separation Science and Technology, 2004, pp. 2915-2930 vol. 39, No. 12.
Watkins et al., The Role of the Electrical Double Layer and Ion Pairing on the Electrochemical Oxidation of Hexachloroiridate (III) at Pt Electrodes of Nanometer Dimensions, Langmuir, May 25, 2004, pp. 5474-5483, vol. 20.
Han et al., Continuous Magnetophoretic Separation of Blood Cells in Microdevice Format, Journel of Applied Phyics, Nov. 15, 2004, pp. 5797-5802, vol. 96, No. 10.
Chen et al., Probing Single DNA Molecule Transport Using Fabricated Nanopores, Nano Letters Oct. 26, 2004, pp. 2293-2298, vol. 4, No. 11.
Blums, New Problems of Particle Transfer in Ferrocolloids: Magnetic Soret Effect and Thermoosmosis, The European Physical Journal E, Nov. 16, 2004, pp. 271-276, vol. 15.
Arrigan, Nanoelectrodes, Nanoelectrode Arrays and Their Applications, The Analyst, Nov. 9, 2004, pp. 1157-1165, vol. 129.
Neuberger et al., Superparamagnetic Nanoparticles for Biomedical Applications: Possibilities and Limitations of a New Drug Delivery System, Journel of Magnetism and Magnetic Materials, Mar. 2, 2005, pp. 483-496, vol. 293.
Akeson et al., Microsecond Time-scale Discrimination Among Polycytidylic Acid, Polyadenylic Acid, and Polyuridylic Acid as Homopolymers or as Segments Within Single RNA Molecules, Biophysical Journal, Dec. 1999, pp. 3227-3233, vol. 77.

* cited by examiner

*Primary Examiner* — Suryaprabha Chunduru
(74) *Attorney, Agent, or Firm* — Black Lowe & Graham, PLLC

(57) ABSTRACT

The invention provides labels for electronic detection of individual molecules. The labels are comprised of elements with different electrical properties that affect the electric current flowing through a nanoelectrode. The labels are of polymeric or filamentous structure where the elements are arranged linearly along their length. The arrangement of the elements is predetermined and combinatorial, so that a high diversity of labels can be generated in a manner that resembles barcoding on a nanoscale level. Methods for the synthesis of said barcode labels and for the binding of the barcode labels to individual molecules, their movement past a nanoelectrode, and their detection are also provided.

18 Claims, 5 Drawing Sheets

LABELS FOR ELECTRONIC DETECTION OF INDIVIDUAL MOLECULES AND METHODS FOR THEIR DETECTION

PRIORITY CLAIM

This application is related to and claims the benefit of U.S. Provisional Application 60/814,377 filed Jun. 15, 2006, the disclosure of which is incorporated herein by reference in its entirety.

FIELD OF THE INVENTION

The field of the invention is analyte detection, identification and quantification using detectable labels.

BACKGROUND OF THE INVENTION

Analyte detection and quantification is important in many different technical areas such as biomedical research (both in industry and in academia), clinical diagnostics, agricultural diagnostics and practices, environmental control, forensics, personalized medicine, pharmacogenomics, and others.

While some analytes can be detected and measured directly, very often it is useful to detect analytes using attached labels that can be more easily detected and measured. Multiple labels have been developed over the years for various analytical applications: radioisotopes, fluorescent dyes and quantum dots have all been used in analyte labeling. The signal generated by such labels can be detected with appropriate instrumentation. For example, the light emitted by fluorescent dyes upon suitable excitation can be detected and quantified with light measuring devices such as photomultipliers (PMT) or quantitative charge-coupled devices (CCDs).

When the analyte is contained in a complex mixture it needs to be specifically targeted for labeling. This is often accomplished through analyte-specific probes, such as antibodies. For example, when an analyte-specific antibody which is labeled with a fluorescent dye binds to the analyte of interest, the fluorescence associated with the antibody indirectly quantifies the amount of analyte present. Similarly, when an isotopically-labeled DNA probe that is complimentary to an analyte mRNA binds to its target analyte, the radioactivity level that is detected corresponds to the amount of the specific mRNA that is assayed. In these types of applications, the analyte is often referred to as the "target".

In most analytical methods using detectable labels, multiple analyte molecules generate an aggregate signal that is detected simultaneously. Such a mode of quantification is referred to as analog, since it measures an analog value, such as light intensity or level of radioactivity. In contrast, digital techniques would detect each individual molecule (Ishijima and Yanagida 2001) of the analyte separately and tally their counts. Digital techniques offer multiple advantages over analog ones: high sensitivity, high signal-to-noise, high accuracy, and low cost. These advantages stem from the fact that the measurement system does not normally require a precisely calibrated linear response and large dynamic range, as its goal is to only detect the presence or absence of a particular molecule, while the quantification is achieved through tallying the number of times the molecule has been detected (Dimitrov 2001).

Multiparameter or multiplexed detection and quantification simultaneously measures multiple and different species of analyte. For example, in expression profiling, mRNA levels for thousands of different genes can be assayed simultaneously (Schena 2003). Distinct labels for such a large diversity of analytes can be generated through combinatorial assembly of a limited number of detectable elements. Such labels can be called barcodes because they exhibit some aspects of barcode labels widely applied in the retail industry and elsewhere, although they are functionally very different from such barcode labels.

SUMMARY OF THE INVENTION

The present invention provides labels for the electronic detection of individual target molecules, and methods for their synthesis, binding to the target molecule, and electronic detection.

In particular, the present invention provides labels for the electronic detection of individual target analyte molecules comprising a target specific probe capable of binding the target analyte molecule attached to a polymeric molecule or filament, wherein the polymeric molecule or filament comprises one or more elements with different electrical properties as detected by a nanoelectrode. Such labels are hereinafter sometimes referred to as "barcode labels." Target analyte molecules are hereinafter sometimes referred to as "targets," "target analytes" or "target molecules." Target specific probes are hereinafter sometimes referred to as "affinity probes." Polymeric molecules are hereinafter sometimes referred to as "polymer-based filaments." A polymeric molecule or filament (polymeric or otherwise) that contains one or more elements with different electrical properties as detected by a nanoelectrode is sometimes referred to hereinafter as a "NanoTape."

The present invention also provides compositions comprising two or more labels, each of which comprises a target specific probe capable of binding a target analyte molecule attached to a polymeric molecule or filament, wherein the polymeric molecule or filament comprises one or more elements with different electrical properties as detected by a nanoelectrode, and wherein the target specific probe of each label is different from each of the other labels.

The present invention further provides kits for the electronic detection of individual target analyte molecules comprising:
  (a) one or more labels each of which comprises a target specific probe capable of binding the target analyte molecule attached to a polymeric molecule or filament, wherein the polymeric molecule or filament comprises one or more elements with different electrical properties as detected by a nanoelectrode;
  (b) a nanoelectrode capable of detecting the elements with different electrical properties; and
  (c) a redox mediator capable of undergoing redox reactions at a surface of the nanoelectrode.

The present invention additionally provides methods for the detection of individual target analyte molecules in a sample comprising:
  (a) contacting one or more labels, each of which comprises a target specific probe capable of binding the target analyte molecule attached to a polymeric molecule or filament, wherein the polymeric molecule or filament comprises one or more elements with different electrical properties as detected by a nanoelectrode, with a target analyte molecule;
  (b) moving label that is bound to the target analyte molecule sufficiently close to a nanoelectrode such that the electric current of the nanoelectrode is changed; and (c) detecting the changes in electric current produced in the nanoelectrode by the elements with different electrical properties in label that is bound to the target analyte molecule.

The barcode labels of the present invention have two essential components: an affinity probe used for binding the label to a target molecule or a sequence, and a polymer-based filament that contains elements with different electrical properties, hereinafter sometimes referred to as a "nanoTape." The labels are detected by passing them by a detecting nanoelectrode. Depending on the target molecule to be detected, various affinity probes can be used. For example, the affinity probe can be a nucleic acid complimentary to the target molecule, a nucleic acid mimetic (Demidov 2003), a nucleic acid aptamer (Stoltenburg, Reinemann et al. 2005), an antibody, a receptor, a ligand, a lecitin molecule, or any other type of molecule that is involved in molecular recognition and affinity binding to a target analyte.

The nanoTape is a polymer-based or other filament that contains elements with different electrical properties. The specific order of the elements is predetermined for each nanoTape and specifically encodes the identity of the barcode label. As the nanoTape is passed by a nanoelectrode, it is read in a fashion similar to the way magnetic tape is read by a computer tape drive: each element is identified as a bit of information and the bit-sequence of the elements encoded on the nanoTape uniquely identifies the corresponding barcode label and hence the underlying target analyte molecule to which it is bound. The process of passing a label or a nanoTape by a nanoelectrode is hereinafter sometimes referred to as "streaming."

In one embodiment of the invention, the nanoTape is a DNA molecule that contains branched structures at specific, predetermined positions along its length. The branched structures are electroactive elements that hinder the diffusive transport of redox mediators to the nanoelectrode thus affecting the current that flows through the nanoelectrode. In a particular embodiment, the branched elements are created and attached via streptavidin-biotin interactions that are well-established in the art.

In a preferred embodiment two barcode labels are used to bind and detect a single target molecule or sequence, forming a composite barcode label. Use of dual labels offers multiple advantages, such as: creating a large diversity of composite barcodes from a limited number of single barcode labels, reducing the false positive rate, eliminating the need for removal of unbound barcode labels, facilitating separation of bound from unbound probes, and individually targeting specific domains in target molecules.

A nanoelectrode is used in the present invention to detect barcode labels bound by a target analyte. In general, the nanoelectrode should be as small as or smaller in size than the electroactive element to be detected. In one embodiment, the nanoelectrode has a critical dimension (as determined by the length of its longest dimension, such as its diagonal in the case of a rectangular nanoelectrode or its diameter in the case of a circular nanoelectrode) of about 20 nm to about 100 nm. In another embodiment, the nanoelectrode has a critical dimension of less than about 100 nm. Such a nanoelectrode can be fabricated on a chip (silicon, glass, or plastic) using standard micro- or nanofabrication techniques. State-of-the-art photolithography allows for features as small as 65 nm to be fabricated. Alternatively, the chip containing the nanoelectrodes can be fabricated through a combination of photolithography and nanolithography methods, such as high resolution E-beam lithography, or other nanolithographic techniques. In a preferred embodiment of the invention, an array of multiple individually addressed nanoelectrodes is fabricated to improve the throughput of detection.

The surface of the nanoelectrode is exposed to a solution containing an electrolyte and a redox compound (mediator). In one embodiment, a channel within a chip contains the solution containing an electrolyte and a redox compound. In general, a good redox mediator will have high kinetic constants (fast electron transfer), low redox potential, reversible electrochemistry and good stability. For example, ferrocene carboxylic acid is a suitable redox compound for embodiments where the nanoelectrode is an anode and the nanoTape is a negatively charged polymer, such as DNA. Redox reactions involving the mediator provide the flow of electrons through the nanoelectrode; the rate of such flow is affected by the nearby passage of the nanoTape containing electroactive elements.

Individual target molecules that bind barcode labels are moved (streamed) along the length of the channel containing the nanoelectrodes. In a preferred embodiment, two barcode labels per target molecule are used (designated Left and Right for illustration purposes). The ends on the nanoTape that are opposite to the end where the target specific probe is conjugated (designated as the left end of the Left barcode label and the right end of the Right barcode label for illustrative purposes as shown in FIG. 1B) can be modified in a manner that facilitates the stretching, movement and purification of the dual barcode labels that are bound by a target molecule. The process of uncoiling a polymeric molecule or filament such as a long DNA molecule is hereinafter sometimes referred to as "stretching."

In a preferred embodiment of the invention, the left end of the Left barcode label is modified using a magnetic nanosphere. Magnetic forces act on the nanosphere to move it through the channel while the nanosphere itself pulls the [barcode label-target molecule] complex through the channel. In another embodiment, the right end of the Right label can be modified so that a force is exerted in the opposite direction to the force moving the [barcode label-target molecule] complex in order to facilitate stretching of the complex as it passes by the nanoelectrode.

As the nanoTape of the barcode labels passes through the channel containing the nanoelectrodes, the elements on the nanoTape cause changes in the electric current flowing through the nanoelectrode. In an illustrative embodiment, the branched elements on a DNA-based nanoTape interfere with the mass transport of redox mediator to the surface of the nanoelectrode, thereby effectively reducing the conductance of the nanoelectrode (increases the resistance) and thus reducing the current through it.

The drop in the current is detected with an appropriate detection device capable of detecting current changes of this magnitude, such as a low-noise, high bandwidth electronic amplifier/amperometer. Alternatively, the changes in the resistance of the nanoelectrode connection can gate a transistor that is fabricated in the chip, thus greatly increasing the strength of the output signal.

Since the purpose of detection is discrimination between the positive and negative elements on the nanoTape ("1"s and "0"s), the system can tolerate large distortion from linear amplification. In other words, the linearity and the dynamic range of the amplifier can be traded off for greater gain and speed (bandwidth).

DETAILED DESCRIPTION OF THE PREFERRED EMBODIMENT

A. Barcode Labels

The barcode labels that are subject of the present invention are individually detectable and can bind to no more than one target molecule, thus making them monovalent and ensuring that individual target molecules are detected.

Each barcode label is comprised of at least two distinct parts: an affinity probe that binds to the target analyte and a stretch of nanoTape that can be detected, that is "read," by a nanoelectrode. Each nanoTape is comprised of elements with different electrical properties. The diversity of the barcode labels is generated through linear combinatorial assembly of the elements. The elements can be detected when they pass by a stationary nanoelectrode; each barcode label is characterized by the sequence of elements detected by the nanoelectrode.

The barcode labels can also include components that facilitate different characteristics of the barcode labels, such as their movement, stretching and purification. In a preferred embodiment such component is a magnetic nanosphere attached to the end of the nanoTape that is opposite to the affinity probe. Additional elements that can be attached to that end of the NanoTape include, for example, diamagnetic nanospheres, cholesteryl moieties, protein molecules, protein complexes or other affinity tags or nanoparticles that would facilitate the movement and stretching of the barcode label.

Figure 1A:
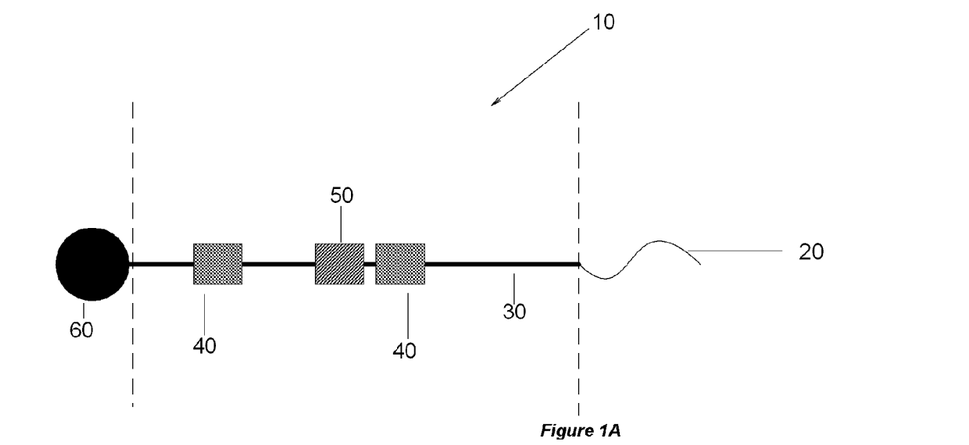
FIG. 1A shows a schematic representation of a barcode label with its main components.
Figure 1B:
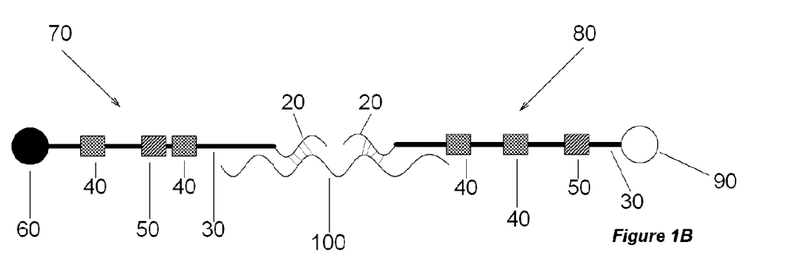
FIG. 1B shows a schematic representation of a dual barcode label bound to a target molecule.

FIG. 1A is a schematic representation of an exemplary embodiment of a label 10 of the present invention comprising a target specific probe 20 attached to a polymeric molecule 30 which contains a first alternating element 40 and a second alternating element 50 with different electrical properties. The exemplary embodiment of the label 10 also contains a magnetic nanosphere 60 attached to the end of the polymeric molecule 30 opposite that of the target specific probe 20.

1. Affinity Probe

The affinity probe is used to bind the barcode label to a target analyte. In this context, "bind," "bound" and "binding" refer to attachment of an affinity probe to a target analyte. In general, the affinity probe will bind to a target analyte selectively, that is, the affinity probe will preferentially bind a target analyte selectively with little or no detectable binding activity towards other molecules.

The target analyte can be any molecule the presence of which is desired to be measured. Exemplary target analytes include, for example, nucleic acids, including single or double stranded DNA or RNA molecules, such as genomic DNA, cDNA and mRNA. Such target nucleic acids can be of synthetic or natural origin, can be of linear, circular or branched configuration and can represent either the sense or antisense strand, or both, of a native nucleic acid molecule. Other exemplary target analytes include, for example, proteins, polypeptides, polysaccharides, carbohydrates, lipids and small organic molecules. In general, the target analyte can be any molecule for which a target specific probe exists or can be prepared. A target analyte can be the sole or major component of a sample or part of a sample that contains other components, such as whole cell or tissue samples, cell or tissue extracts or cell or tissue lysates. Target analytes can also be detected in mixtures which contain multiple different target analytes or only one type of analyte. Further, the target analyte can have either an unknown or known structure or sequence.

In general, the affinity probe will be selected based on the target molecule to be detected. For example, if the target analyte is a nucleic acid, such as RNA or DNA, then the affinity probe can be a complimentary oligonucleotide, or a oligonucleotide mimetic such as a peptide-nucleic acid (PNA), or a locked nucleic acid (LNA)(Orum and Wengel 2001; Demidov 2003), that would bind to the target molecule through the well-known process of hybridization (Tijssen 1993).

As a further example, if the target analyte is a protein, polysaccharide, lipid or a small molecule, then the affinity probe can be an antibody or another protein, or a nucleic acid aptamer with affinity to the target. Other affinity probes include, for example, receptors, ligands and lecitin molecules or any other type of molecule that is involved in molecular recognition and affinity binding to a target analyte.

The affinity probe is attached to the NanoTape using methods that are applicable to the chemical nature of the probe and the nanoTape. There are a wide variety of conjugation and ligation techniques that are available for one skilled in the arts to carry out such attachments. For example if the nanoTape is DNA-based and the probe is an oligonucleotide, then the two can be joined together by enzymatic ligation. As another example, if the nanoTape is DNA-based and the probe is protein based, then the probe can be conjugated to an amino-modified terminal base in the DNA-based NanoTape. As a further example, if the nanoTape is a polymer other than DNA, it can be terminated with a chemically reactive group that would allow conjugation to a protein nucleic acid based probe. Attachment of the affinity probe to one end of a linear polymer ensures a 1:1 stoicheometry with the nanoTape, thus making the barcode label monovalent.

Binding of the affinity probes to target analytes can be performed using procedures, such as hybridization, that are extensively described in the art. Such procedures are discussed, for example, in Hames and Higgins. Nucleic Acids research Hybridization: A Practical Approach, IRL Press, Oxford (1991) and Current Protocols in Molecular Biology (ed. Ausubel et al., Greene Publ., New York 1989, both of which are incorporated by reference herein.

2. Nanotape

The nanoTape is a critical part of the present invention; it is a polymeric molecule or filament that contains elements with different electrical properties. In general, the NanoTape can be any polymer or filamentous nanostructure which contains or which can be modified to contain one or more and up to about six distinct functionalities with different electrical properties at multiple precise positions along the polymer chain. The specific order of the elements is predetermined for each nanoTape and specifically encodes the identity of the barcode label. As the nanoTape is streamed by a nanoelectrode, it is read in a fashion similar to the way magnetic tape is read by a tape drive; each element is identified as a bit of information and the bit-sequence of the elements encoded on the nanoTape uniquely identifies the corresponding barcode label and hence the underlying target analyte molecule to which it is bound. The number of possible combinations (N) equals the number of distinct functionalities with different electrical properties (a) to the power of positions available on the nanoTape(n):

$N=a^n$, so that for example a nanoTape with two different functionalities (two-bits) and eight positions can encode $2^8=256$ different combinations.

In a preferred embodiment, the nanoTape contains two different elements, hereinafter sometimes referred to as "bulky" elements and "slim" elements. The "bulky" elements would occlude the nanoelectrode, thereby causing a decrease in diffusion/migration of a redox mediator compound to its surface, which in turn causes a decrease in current (see discussion below). The "slim" elements would not obstruct the nanoelectrode and would allow more efficient mass transfer to the nanoelectrode surface. In an exemplary embodiment, the "slim" element is the polymer linker that connects the bulky elements (the straight line between the shaded squares in FIGS. 1a, 1b, 1c and 2). Therefore, the "bulky" and "slim" elements would produce two distinctly different current levels through the nanoelectrode, which can be assigned the value of "1" and "0" respectively. Reading the nanoTape would thus produce a distinct sequence of "1"s and "0"s, similar to the binary information read from magnetic tapes or other digital information carriers.

Suitable polymers which can be used for the NanoTape include, for example, DNA, RNA, proteins, peptides and polyacrylic copolymers. Filaments not commonly referred to as polymers, such as silicon nanowires and carbon nanotubes, can also be used for the NanoTape. In a preferred embodiment the nanoTape is based on a DNA polymer. In this embodiment, specific sites in the DNA are modified to contain an affinity tag. Such affinity tags and methods of modifying DNA molecules with them are well-known in the art and include, for example, biotin. The affinity tags can then be used as binding sites for the "bulky" elements. For example, when the affinity tag is biotin, straptavidin-coated nanoparticles (available from various vendors such as G. Kisker or others) that would bind specifically to the biotin residues can be used as the bulky element. In an alternative embodiment when the affinity tag is biotin, the bulky element can be the streptavidin-DNA complex as shown in FIG. 4C.

3. Two Barcodes Per Target

The invention also provides for the use of two or more barcode labels per molecule of target analyte. Each of the barcode labels has a different affinity probe and a nanoTape associated with it. The affinity probes are targeted towards different segments of the target analyte. For example, if the target analyte is a nucleic acid molecule, the affinity probes would bind to different sequences within the molecule. As another example, if the target analyte is a protein the affinity probes would bind to different domains or epitopes of the protein.

For illustrative purposes, when two barcode labels per target molecule are used, they will be named as a Left label and a Right label. As a complex containing the two barcode labels bridged by a target analyte is formed, the two nanoTapes are in close proximity and are read by the nanoelectrode as a single composite barcode.

FIG. 1B is a schematic representation of an exemplary embodiment of the present invention showing two labels bound to a target molecule. The first or Left label 70 comprises, as set forth above, the target specific probe 20 attached to the polymeric molecule 30 which contains the first element 40 and the second element 50, and the magnetic nanosphere 60. The second or Right label 80 comprises, as set forth above, the target specific probe 20 attached to the polymeric molecule 30 which contains the first element 40 and the second element 50. The second or Right label 80 also contains a diamagnetic nanosphere 90 attached to the end of the polymeric molecule 30 opposite that of the target specific probe 20. The target specific probe 20 of the Left label 70 binds to a different portion of the target molecule 100 than the target specific probe 20 of the Right label 80. The Left label 70 and the Right label 80 also have different electrical properties since the arrangement and location of the first element 40 and the second element 50 in the polymeric molecule 30 of the Left label 70 and the Right label 80 are different.

Use of two barcode labels per target molecule provides one or more of the following advantages over a single label:

(i) Creating a large diversity of composite barcodes from a limited number of single barcode labels. Since each composite barcode is composed of the pair-wise combination of two single barcode labels, a population of n specifiers each used in a "left" and a "right" configuration can encode $n^2$ different barcodes. For example, if 256 different single barcode labels are used in pairwise combinations they can encode more than 65,000 ($256^2$) composite barcodes, sufficient to distinctly label transcripts from each gene in the human genome, for example.

(ii) Reducing the false positive rate. In order for a target molecule to be positively identified by this method it needs to bind two independent affinity probes at the same time. The average false positive rate (f) of nonspecific binding of probe to target is:

$$f=FP/(FP+TP)<1$$

where FP is the number of false positive identifications and TP is the number of true positive identifications. Using dual barcode labels makes the false positive rate to be $f*f=f^2$. For example, if 1% of all binding events are nonspecific binding of probe to target, the false positive identification rate for dual probes would be 0.01% (($1\%)^2$).

(iii) Eliminating the need for removal of unbound barcode labels. Since the target molecule itself may be undetectable by the nanoelectrode, separation of barcodes bound to target from empty barcodes is required, as otherwise the latter would be detected and falsely identified. Use of dual barcodes formally eliminates the need for separation, as binding of target leads to dimerization of barcode labels, giving rise to composite barcodes that are twice as long, and hence easily distinguishable, from the single barcode labels that are not bound to a target.

(iv) Facilitating separation of bound from unbound probes. From a practical consideration, separation of bound from unbound labels is still desirable. In practicing the present invention, the labels are typically added in excess to the targets to drive up the binding kinetics as well as to ensure a dynamic range of the system by avoiding saturation of probes with target. Therefore, if large excesses of unbound labels are not removed, they would overwhelm the system, making it difficult to identify the composite barcode labels.

Use of multiple labels per target analyte can be used to facilitate the separation of bound from unbound labels. This can be implemented via at least two possible mechanisms.

(a) Size-based Separation.

The two or more barcode labels bound to a single target molecule form a complex with a molecular weight exceeding the molecular weight of a single label. Thus, such a complex can be separated from the single unbound labels by size-based separation techniques, including, for example, electrophoresis, chromatography, ultrafiltration, or ultracentrifugation.

(b) Affinity Based Separation.

When two or more labels are bound to a target they can be formally split into groups, for example, "left" and "right". Labels from each group can be labeled with a specific affinity tag and then a series of affinity-based separation techniques can be used to separate complexes that have a full complement of labels ("left"+"right") from single labels not bound to target, or complexes with less than full complement of labels (only "left" or "right").

(v) Individual targeting of specific domains in biomolecules. Use of multiple labels allows individual domains in a particular analyte molecule to be targeted with domain-specific probes. For example, mammalian mRNAs are assembled from sets of individual blocks, called exons, through a process called splicing. A single gene can give rise to multiple distinct mRNAs by alternative inclusion and exclusion of various exons: alternative splicing. Using dual labels per individual mRNA molecule allows distinct probes for the various exons to be used so that the final readout is the combination of the labels. The advantages of this approach over using a single probe per molecule are two-fold:

(a) Only a limited set of probes corresponding to the number of alternative exons needs to be manufactured in order to cover a vast diversity of possible mRNA splice variants.

(b) Since different mRNA splice variants from the same gene share significant amount of sequence from common exons, it is very difficult if not impossible to design single probes that can distinguish between the variants; using multiple probes only requires the distinguishing of individual exons.

B. NanoElectrodes

A nanoelectrode is used in the present invention to detect barcode labels bound by a target analyte. In general, the critical dimension of the nanoelectrode should be as small or smaller in size than the electroactive element to be detected. The critical dimension is determined by the length of the nanoelectrode's longest dimension, such as its diagonal in the case of a rectangular nanoelectrode or its diameter in the case of a circular nanoelectrode. In one embodiment, the nanoelectrode has a critical dimension of about 20 nm to about 100 nm. In another embodiment, the nanoelectrode has a critical dimension of less than about 100 nm. Such electrodes can be fabricated onto silicon, glass or plastic chips using standard photolithography or nanolithography techniques. Commercial photolithography technology currently operates at a maximum resolution of 65 nm using a deep ultraviolet (DUV) process with a 193 nm wavelength. A type of photolithography called liquid immersion lithography using the 193 nm DUV process has been demonstrated to produce features in the 30-50 nm range.

Nanolithography methods differ from standard photolithography and can routinely produce sub- 100 nm features (Gates, Xu et al. 2004; Onclin, Ravoo et al. 2005; Tseng, Notargiacomo et al. 2005; Garcia, Martinez et al. 2006). A type of nanolithography called E-beam direct lithography has a resolution of ~20 nm. Another type of nanolithography called nanoimprint lithography offers high-throughput reproduction of a template on a substrate and has a resolution of 20 nm or less.

For the purposes of this invention, the dimension of the nanoelectrode is more important than its geometry. The simplest lithographic feature (a dot) would suffice as long as its dimensions are comparable or less than the electroactive element to be detected. Therefore a lithographic process with rated resolution that is above the required threshold can still be modified to produce smaller nanoelectrodes that are functional (see, for example, Watanabe 2005).

The nanoelectrode is preferably fabricated from gold, platinum or copper, although carbon nanotube nanoelectrodes could also be used (Haffier, Cheung et al. 2001; Esplandiu, Bittner et al. 2004). The nanoelectrode is exposed to an electrolyte solution containing the barcode labels and is connected through an electrically insulated lead, to a measurement instrument. The leads are insulated using standard microfabrication techniques and insulating materials such as silicon dioxide.

Current flows from the nanoelectrode(s), through the leads, to the measurement instrument. The circuit is completed by a counter-electrode that is also exposed to the electrolyte solution.

Figure 1C:
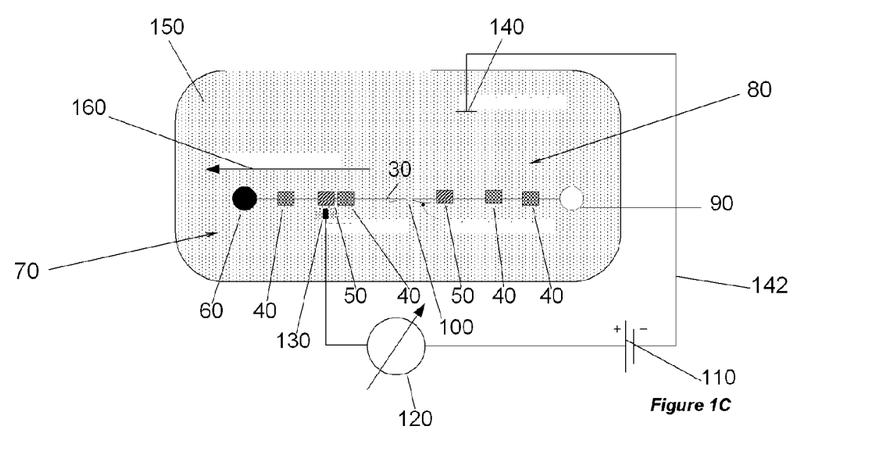
FIG. 1C shows a schematic representation of electronic detection of dual barcode labels. The electric circuit contains a voltage supply, an amperometer, a nanoelectrode, a counterelectrode, and a liquid junction comprising an electrolyte and a redox compound).

FIG. 1C is a schematic representation of an exemplary embodiment of the present invention showing the electronic detection of two labels bound to a target molecule 100. As set forth above, the first or Left label 70 comprises the target specific probe (not shown) attached to the polymeric molecule 30 which contains the first element 40, the second element 50, and the magnetic nanosphere 60, and the second or Right label 80 comprises the target specific probe (not shown) attached to the polymeric molecule 30 which contains the first element 40, the second element 50 and the diamagnetic nanosphere 70. As set forth above, the target specific probe of the Left label 70 binds to a different portion of the target molecule 100 than the target specific probe of the Right label 80. The electric circuit contains a voltage supply 110, an amperometer 120, a nanoelectrode 130, a counterelectrode 140, a lead 142 and a liquid junction 150 comprising an electrolyte and a redox compound. The electric circuit detects current changes in the nanoelectrode 130 caused by the first alternating element 40 and the second alternating element 50 contained in the Left label 70 and the Right label 80 bound to the target molecule 100 as the elements are streamed past the nanoelectrode 130 in the streaming direction 160.

Electrochemical currents through electrode surfaces are diffusion limited: the rate of the reaction is not limited by the electron transfer, but rather by the diffusion of the redox species to the electrode surface (see Section C below). The nanometer dimensions of the nanolectrode provide for very fast radial diffusion of the redox mediator to the electrode and hence high current densities. In addition, the fast radial diffusion inhibits the formation of an advancing depletion layer, which creates steady-state or quasi-steady state conditions (Arrigan 2004).

In a preferred embodiment of the invention, multiple individually addressable nanoelectrodes are fabricated to form an array. Using an array of nanoelectrodes offers several advantages:

(i) Streaming the barcode labels past an array of nanoelectrodes allows the channel containing them to be significantly wider than the nanoelectrode dimensions, while still ensuring that the majority of the labels would be detected. While an individual nanolectrode can be fabricated in a very narrow channel so that the majority of barcode labels still pass through it, such a narrow channel could potentially cause problems with clogging and impeded stream flow.

(ii) The array of nanoelectrodes provides for higher throughput of barcode label detection as multiple barcodes can be detected simultaneously.

It should be stressed that each nanoelectrode in the array is individually connected to the measurement instrument and therefore such array differs from other nanoelectrode arrays that are reported in the literature that act as a single electrode in an electric circuit (Koehne, Li et al. 2003; Koehne, Li et al. 2004).

The pitch (i.e., distance) at which the nanoelectrodes are spaced can be significantly larger than their dimensions (upwards to 10 microns) if the electric field that they create is used to direct the barcode labels to the nanoelectrode. Because of the small dimensions of the nanoelectrode, the electric field is extremely strong in its vicinity and weakens sharply away from it. If electrically charged nanoTape is used in the barcode labels (for example DNA-based nanoTape, which is negatively charged), they can be attracted to the nanoelectrode as they pass in the channel. The force with which these barcode labels will be attracted and focused on the nanoelecrtode depends on several factors that can be controlled in designing a system: ionic strength of the electrolyte, potential (voltage) of the nanoelectrode, geometry of the electric field as defined by the geometry and positioning of the counter electrode, and charge density of the electric charges on the nanoTape.

In addition to such electrophoretic guiding, the barcode labels can be guided to the individual nanoelectrodes through guiding structural features that are fabricated on the surface of the chip, such as: tracks, channels or arrays of posts or pillars (Mannion, Reccius et al., 2006).

C. Electrolyte and Redox System

The barcode-labels described here are detected in an electrolyte solution in which the nanoelectrode(s) and the counter-electrode are immersed. The nanoelectrode(s), the counter-electrode and the electrolyte solution constitute an electric circuit. The counter electrode does not need to have nanometer dimensions. For the circuit to be completed, redox-reactions must take place at the electrode surfaces. This is preferably accomplished via soluble redox mediators present in the electrolyte that undergo redox reactions at the electrodes.

In general, a good redox mediator will have high kinetic constants (fast electron transfer), low redox potential, reversible electrochemistry and good stability. The low redox potential allows for low voltages to be used in the system, thus preventing interfering redox reactions. Examples of unwanted interfering reactions are: (i) electrolysis of water which can create gas bubbles of hydrogen or oxygen; (ii) if a DNA-based nanoTape is used or if the target analyte is DNA, using high electrode voltage should be avoided to prevent interfering oxidation of guanine or adenine nucleic acid bases; and (iii), using high voltage could cause current leakage through the insulated leads that connect the nanoelectrode to the measurement instrument. A list of possible redox compounds, with their standard redox potentials, is shown in the following table.

| Redox Mediator | Redox Potential vs. SCE |
|---|---|
| 1,4-benzoquinone | 39 |
| ferrocene carboxylic acid | 275 |
| phenazine methosulphate | −161 |
| tetrathiofulvalene | 300 |
| tetracyanoquinodimethane | 127 |
| Ferrocyanide ions, $[Fe(CN)_6]^{4-}$ | 180 |
| dimethylviologen | −681 |
| 1,1'-dimethylferrocene | 100 |
| phenazine ethosulfate | −172 |
| ferrocenylmethanol | 185 |

For amperometric detection of the barcode labels the nanoelectrode system must operate at a quasi steady-state (the nanoelectrode current must be constant with time) and provide high current densities when unobstructed by the nanoTape. For fast and reversible electron-transfer mediators this would translate into having a constant flux of mediator to the nanoelectrode surface. The flux is a function of several factors: initial concentration of the mediator, diffusion rate, electromigration, electrode geometry, and regeneration rate, and must be calibrated empirically. One advantage of using nanoelectrodes is that, because of their small critical dimension, diffusion towards the nanoelectrode is radial and therefore very fast. Electromigration depends on the charge of the redox mediator and the nature and concentration of the supporting electrolyte (Ciszkowska, Stojek et al. 1995; Rooney, Coomber et al. 2000; Stevens, Rooney et al. 2001).

Without electromigration, the current through a nanoelectrode with an inlaid disc geometry is given by the formula (Arrigan 2004):

$$I_{lim} = 4nFDc^b r$$

where $I_{lim}$ is the steady state current, D and $c^b$ are the diffusion coefficient and bulk concentration of the electroactive species, F is the Faraday's constant, n is the number of electrons transferred in the redox reaction, and r is the radius of the nanoelectrode.

The redox mediator is regenerated at the counter electrode and therefore the rate of regeneration will depend on the rate of the reverse reaction at the counter electrode. The distance between the nanoelectrode and the counter electrode will also determine how fast the regenerated redox mediator is supplied back to the nanoelectrode. If the regeneration conditions are insufficient to provide an adequate flux to the nanoelectrode, regeneration can be performed in solution. For example if the redox mediator is ferrocene, glucose and glucose-oxidase can be added to the electrolyte so that whatever ferrocene is oxidized by the nanoelectrode it is quickly reduced back by glucose oxidase/glucose (Cass, Davis et al. 1984). Alternatively, if large amounts of electrolyte and redox mediator are used the system can operate for the duration of an analytical procedure without full regeneration. This is possible since due to its small area the nanolectrode will only consume small total amounts of a redox mediator even at high current densities. In general, suitable electrolytes for use in the present invention can be any soluble salt, including, for example, KCl, borate or Tris-Acetate-EDTA (TAE).

D. Streaming

Streaming of the barcode labels containing the nanoTape past the nanoelectrode is important for their detection. The barcode labels need to pass by the nanoelectrode:

(i) one by one;
(ii) in a stretched configuration that allows the consecutive detection of alternating active and passive elements (bits) with different electrical properties; and
(iii) with a velocity commensurate with the ability of the detector to perform such detection.

Various mechanisms exist for moving and stretching individual polymer macromolecules or macromolecular complexes such as the barcode labels complexed to target molecules. These mechanisms can employ, for example, optical tweezers, AC electric fields and hydrodynamic and fluidic forces (Michalet, Ekong et al. 1997; Strick, Allemand et al. 2000; Matsuura, Kurita et al. 2002). In general, the minimum amount of stretching needed is that which allows each electronically active element of the barcode to be separately detected.

In a preferred embodiment the barcode labels of this invention are streamed and stretched using magnetic forces. A single barcode label is tagged with a magnetic nanosphere (MNS) at the end that is opposite to the target-specific probe. When a non-homogeneous magnetic field is applied a magnetic force $F_m$ is exerted on the MNS, given by the formula (Watarai, Suwa et al. 2004):

$$F = -gradU = \frac{(\chi_p - \chi_m)}{\mu_0} V(B \cdot \nabla) \cdot B$$

where, U is the magnetic potential energy of a particle with a volume V and volume magnetic susceptibility $\chi_p$ under a magnetic field B; $\mu_0$ is the vacuum magnetic permeability, and $\chi_m$ is the volume magnetic susceptibility of the surrounding electrolyte.

When $F_m$ is large enough the MNS will move in the direction of the magnetic field gradient. The movement exerts a pulling force $F_{pull}$ that acts on the barcode label. Since the pulling force acts on one end of the nanoTape polymer (i.e., where the MNS is attached), it causes partial stretching of the nanoTape. To achieve full stretching of the barcode label, a pulling force needs to be applied on the other end of the barcode label that is smaller than $F_{pull}$ in magnitude and acts in the opposite direction.

Figure 2:
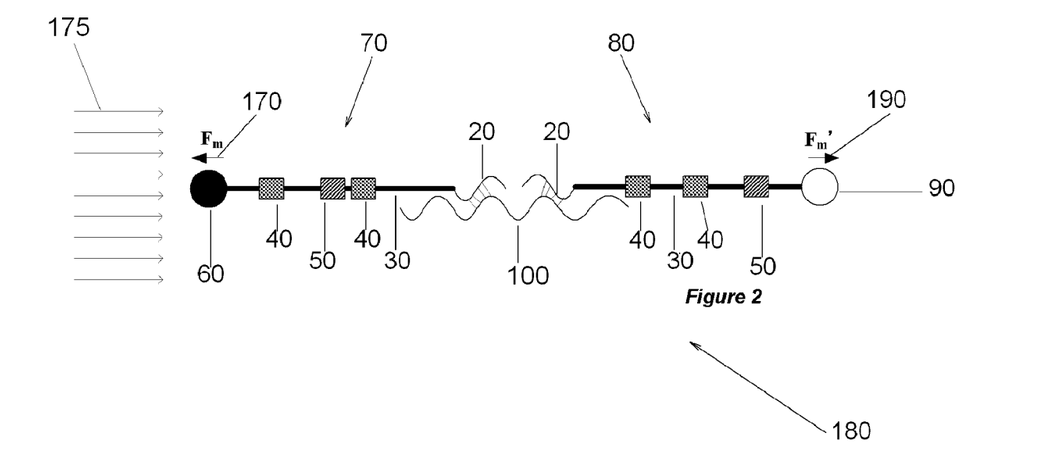
FIG. 2 shows a schematic representation of dual barcode labels (designated for illustrative purposes as Left and Right) tagged with a superparamagnetic nanosphere and a diamagnetic nanosphere, respectively, for streaming and stretching. The superparamagnetic tag can be used to purify the complex containing the barcode labels and the target molecule from any impurities as well as from excess Right labels that are unbound to target. Any unbound Left barcodes will copurify with the complex.

In a preferred embodiment full stretching is achieved with a dual label architecture (see discussion above). FIG. 2 is a schematic representation of an exemplary embodiment of the present invention showing two barcode labels (designated for illustrative purposes as Left and Right) tagged with a superparamagnetic nanosphere and a diamagnetic nanosphere, respectively, for streaming and stretching. As set forth above, the first or Left label 70 comprises the target specific probe 20 attached to the polymeric molecule 30 which contains the first element 40, the second element 50, and the magnetic nanosphere 60, and the second or Right label 80 comprises the target specific probe 20 attached to the polymeric molecule 30 which contains the first element 40 and the second element 50 and the diamagnetic nanosphere 90. As set forth above, the target specific probe 20 of the Left label 70 binds to a different portion of the target molecule 100 than the target specific probe 20 of the Right label 80. In the "Left" label 70, the end opposite of the target specific probe 20 is tagged with the superparamagnetic nanosphere 60, while in the "Right" label 80 the end opposite of the target specific probe 20 is tagged with the diamagnetic nanosphere 90; this end will be called the "tail". The magnetic susceptibility of the superparamagnetic nanosphere 60 is significantly higher than that of the surrounding electrolyte $[\chi_p \gg \chi_m; (\chi_p - \chi_m) > 0]$, while that of the diamagnetic nanosphere 90 is slightly below it $\{\chi_p < \chi_m; (\chi_p - \chi_m) < 0\}$. As a result a strong magnetic force $(F_m)$ 170 generated by a magnetic field gradient 175 acting on the superparamagnetic particle 60 that will pull the "left label"-target-"right label" complex 180 in the direction of the magnetic field gradient. A weaker magnetic force $(F_m')$ 190 acts on the diamagnetic particle 90 that will pull the "tail" end of the complex 180 in the opposite direction thus resulting in stretching of the complex 180 as it passes by the nanoelectrode. In addition, as the complex increases its velocity, a hydrodynamic dragging force will also contribute to the stretching of the complex. The dragging force is given by the formula:

$$\overline{F}_d = 6\pi\eta b \overline{U}$$

where $\eta$ is the dynamic viscosity of the media, b is the particle radius, and U is the velocity in m/s In an alternative embodiment, stretching is achieved by tagging the "tail" end of the "Right" label with a hydrophobic moiety, such as cholesterol and palmitoyl, using any of a variety of available modification chemistries, and the surface of the channel that contains the nanoelectrode is made hydrophobic, for example by silanization with octadecylsilane. The cholesteryl moiety interacts with the hydrophobic surface through Van der Walls interactions resulting in a dragging force that is exerted on the 'tail' end.

Superparamagnetic and paramagnetic, as well as diamagnetic (for example, polystyrene) nanospheres, are commercially available with various surface chemistries that allow attachment to one end of a nanoTape. For example, superparamagnetic and paramagnetic particles and nanospheres can be constructed using metal oxides.

In a preferred embodiment the nanoelectrode(s) are on the bottom of a channel. In general, for the invention to work, it is important that the barcode labels are streamed close enough to the bottom surface of the channel so that they are able to impact the electric current of the nanoelectrode (typically less than one micron from the surface); if they are to float substantially higher they would not be able to impact the electric current of the nanoelectrode. In order to fulfill this requirement, it is preferred that the barcode label complexes settle on the surface of the channel prior to their passage by the nanoelectrode. The MNS facilitates this process. In addition to the magnetic forces, a gravity force is also exerted on the tagging nanospheres that lead to their settling on the bottom of the channel containing the nanoelectrode.

If the hydrophobic "tail" tagging described above is used it would create additional enrichment of the barcode labels near the surface because of hydrophobic and Van der Walls interactions with the bottom surface of the channel.

In a preferred embodiment the barcode labels contain an electric charge embedded in the nanoTape that is used to pull them towards the nanoelectrode once they reach its close vicinity, due to the high density electric field described in Section B above.

E. Detection

As the stretched barcode labels are streamed past the nanoelectrode, the changes in the nanoelectrode current caused by the passage of the alternating electroactive elements of the barcode are propagated through the leads and detected by a detection instrument. Thus the spatial information encoded along the length of the barcode label is translated into time-domain information detected by the instrument.

In a preferred embodiment, where the signal being detected is current, the detector is a galvanometer with an electronic amplifier. In general, the amplifier must be able to detect low amplitude, high bandwidth signals. If the signal that is measured is current, it is in the 100 pA-10 nA range. The bandwidth of a signal is a measure of how rapidly it fluctuates with respect to time. Hence, the greater the bandwidth, the faster the variation in the signal may be. The Nyquist sampling theorem states that discrete samples are a complete representation of the signal if the bandwidth is less than half the sampling rate, which is referred to as the Nyquist frequency. Therefore the frequency at which the instrument samples the signal must be greater than twice the frequency at which the signal changes with time.

It follows from the preceding paragraph that there are tradeoffs that need to be considered in designing a system. If the bandwidth of the detection instrument is limited, then the signal frequency must be decreased. The signal frequency is the frequency at which the alternating elements (bits) pass by the nanoelectrode. Each element will affect the nanoelectrode current for a specified time $T_R$ (residence time):

$$T_R = \frac{L}{V}$$

where L is the length of the element in nanometers and V is the velocity with which the barcode label passes by the nanoelectrode. The minimum resident time required for efficient sampling is given by $$T_R = \frac{s}{f_s}$$

where $f_s$ is the sampling frequency and s is the number of samples taken per bit (must be larger than two). Suitable commercially available detector instruments, for example the Axiopatch available from Molecular Devices, can be used to sample at a 300 kHz sampling frequency ($f_s$=300 kHz). In this case, for each element of the nanoTape, the minimum resident time required to take three samples (s=3) in order to satisfy the Nyquist theorem, is 10 microseconds.

$T_R$ can be adjusted by varying L (making longer or shorter elements of the nanoTape) or V (by adjusting the forces that act on the barcode label).

In situations where the nanoelectrode is used to attract an electrically charged nanoTape, the different alternating elements (the "1"s and the "0"s) may have different "stickiness" to the nanoelectrode due to a difference in their volumetric charge density. In that case the residence time of each of the element types can be adjusted separately.

There is a tradeoff in electronic amplifiers between the amplitude of the detected signal and its bandwidth. Amplifiers for low-level signals are limited in bandwidth and vice versa. Because the nanoelectrode has a very small area the total current going through it will always be low, regardless of how high the achieved current densities are. This makes the requirements on the detector demanding. An additional demand on the instrument is introduced if a nanoelectrode array is used. In that situation the instrument has to detect the signal from each individual nanoelectrode in the array, which means that it needs multiple channels.

The demands on the detector instrument can be reduced by incorporating electronic components in the same chip that contains the nanoelectrodes. This is accomplished by standard microelectronics fabrication. For example, the signal can be amplified electronically in the chip before reaching the detector instrument. Amplification of the signal in the chip allows a stronger signal to be fed into the detector and hence a simpler detector can be used with significantly higher bandwidth.

Figure 3:
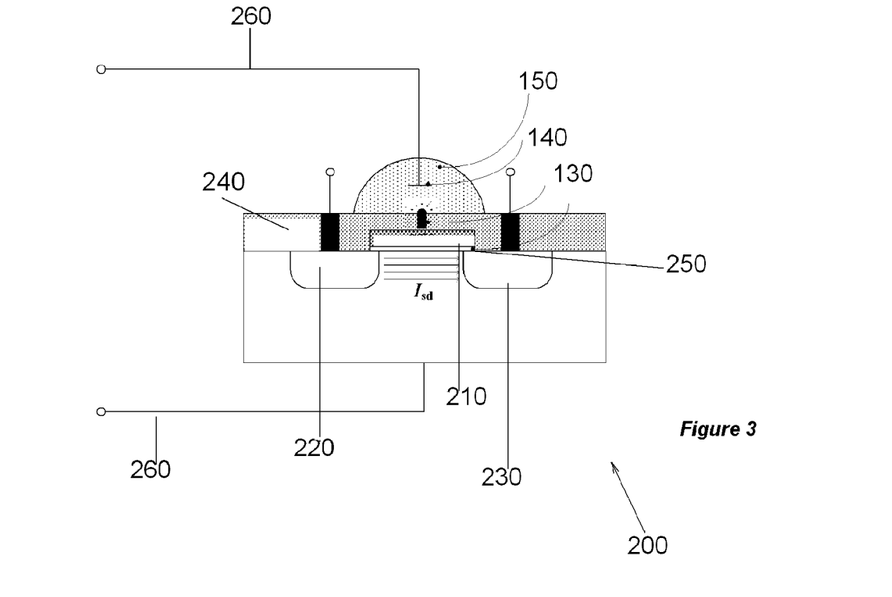
FIG. 3 shows a schematic drawing (side view) of a MOSFET for barcode detection. The supplied gate voltage between the counterelectrode and the body of the transistor is modulated through the changes in conductivity of the electrolyte junction caused by the passage of barcode labels in the vicinity of the nanolectrode. The electrolyte junction is the electrical connection between the nanoelectrode and the counterelectrode (contained in the microchannel in FIG. 5D).

For example, single transistor fabricated in the chip can be used to amplify the signal from the nanoelectrode. In such an implementation the nanoelectrode is connected to the gate of a semiconductor transistor (FIG. 3). This could be a field-effect transistor, such as MOSFET (Metal-Oxide-Semiconductor Field-Effect Transistor) or MESFET (Metal-Semiconductor Field-Effect Transistor). Field Effect Transistors provide high amplification (gain) of a signal, with high bandwidth. MESFETs are better suited for this invention as they require lower gate voltage and higher bandwidth (up to 4 GHz or higher), however their fabrication is less conventional than MOSFETs which are the workhorse of the semiconductor chip industry and which are also well suited for application within the present invention. The most basic amplification scheme is accomplished via a MOSFET. For the purposes of the present invention the input signal is the gate voltage; the gate-nanoelectrode and the counterelectrode are connected through the electrolyte (liquid junction) and the gate voltage varies due to the ohmic drop (I*R) from the changes in current caused by blockage of the gate-nanoelectrode with the nano-Tape. This results in changes in the output signal, which is the source-drain current ($I_{sd}$).

FIG. 3 is a schematic representation of an exemplary embodiment of the present invention showing a MOSFET 200 for label detection. As set forth above, the nanoelectrode 130, the counterelectrode 140 and the liquid junction 150 are shown. The nanoelectrode 130 is connected to a gate 210 of the MOSFET 200. Other portions of the MOSFET 200 that are shown include a source 220, a drain 230, an insulator 240, a metal oxide 250 and leads 260 connecting the MOSFET 200 to the remainder of the circuit.

Field-effect transistors are well suited for digital applications, such as the one described here. Since the goal of detection is to discriminate between the positive and negative elements on the nanoTape ("1" and "0"), large distortions from linear amplification can be tolerated. In other words, the linearity and the dynamic range of the transistor amplifier are traded off for a higher gain and speed (bandwidth). Such tradeoffs are not possible for analog applications where the information is carried in a continuum of signal values.

More elaborate amplification circuits with multiple transistors, as well as other electronic components, such as resistors, capacitors and diodes, can provide even better amplification with minimal incremental cost because of the scaling efficiencies in current microelectronic fabrication.

Other electronic functions that can be integrated into the chip include:

(i) Time-division multiplexing. If the signal is preamplified sufficiently in the chip, then a detector with very high bandwidth can be used (up to 100 MHz or more). Such bandwidth will be excessive for a single nanelectrode and therefore the signal from multiple nanoelectrodes can be merged into a single high bandwidth signal via time division multiplexing. This would allow a single channel in the detector to read the signal from multiple nanoelectrodes in the array.

(ii) "Dead current" logical filter. The barcode labels of this invention are sparsely streamed by the nanoelectrode, in order to prevent overlap, which creates substantial "dead" signal between two barcodes. Detection and recording of such signal is an unnecessary burden on the detector that can be avoided by incorporating a logic integrated circuit (IC) that can discriminate between the "dead" current and the barcodes and pass only the barcode signal to the instrument.

F. Kits

The present invention also contemplates kits for the electronic detection of individual target analyte molecules containing one or more of the components discussed above that are necessary for the practice of the present invention. Such kits can include, for example, one or more of labels, nanoelectrodes, redox mediators and electrolytes. Instructions for use of the kit components can also be included in the kits. In one embodiment, a kit for the electronic detection of individual target analyte molecules comprises one or more labels, a nanoelectrode and a redox mediator, in which the various kit components have the characteristics described above.

G. Applications

It should be apparent that the present invention can be used for analyte detection and quantification in many different technical areas, including biomedical research (both in industry and in academia), clinical diagnostics, agricultural diagnostics and practices, environmental control, forensics, personalized medicine, paternity testing, pharmacogenomics, and others. For example, the present invention can be used to detect and quantify one or more target analytes representative of a particular disease or condition in a sample obtained from a patient. As another example, the present invention can be used to detect and quantify one or more target analytes (e.g. tumor antigens) in a sample obtained from a patient to determine the best course of treatment and therapy for the patient. As a further example, the invention can be used to detect blood-borne pathogens or antibodies against blood-borne pathogens, such as malaria or dengue fever. In other applications, the invention can be used for the detection of specific markers in agricultural breeds. In an additional example, the invention can be used for the detection of specific genetic markers in forensic practice to determine parenthood or the identity of a criminal. All such applications are included within the scope of the present invention.

The following example is for purposes of illustrating certain embodiments of the present invention and is not to be construed as limiting the present disclosure.

EXAMPLE

This example describes dual barcode labels for sixteen different mRNAs, their components, and the procedures for their detection.

A. Barcode Labels

The barcode labels are constructed using DNA of M13mp18 single stranded phage vector obtained from New England Biolabs or other vendors as the scaffold for constructing the nanoTape and for ligation of affinity probe(s) to its ends to make a complete barcode label. This DNA is 7249 bases long and, when linearized, converted into double stranded form, and stretched to its full contour length, it measures about 2,400 nm.

Two barcode labels per target analyte are constructed: left (L) and right (R). Each of the two barcodes contains two bits of information. The combined dual barcode label thus contains four bits that can encode 16 different combinations ($2^4$) that are denoted as follows: L(00)R(00), L(00)R(01), L(00)R(10), L(00)R(11), L(01)R(00), L(01)R(01), L(01)R(10), L(01)R(11), L(10)R(00), L(10)R(01), L(10)R(10), L(10)R(11), L(11)R(00), L(11)R(01), L(11)R(10), L(11)R(11).

1. NanoTape Encoding

A NanoTape based on the M13mp18 vector (DNA based polymer) is prepared. The M13mp18 vector is first linearized by annealing a complimentary oligonucleotide to the region containing the Multiple Cloning Site and digesting with a BamHI restriction endonuclease in a suitable buffer.

Figure 4A:
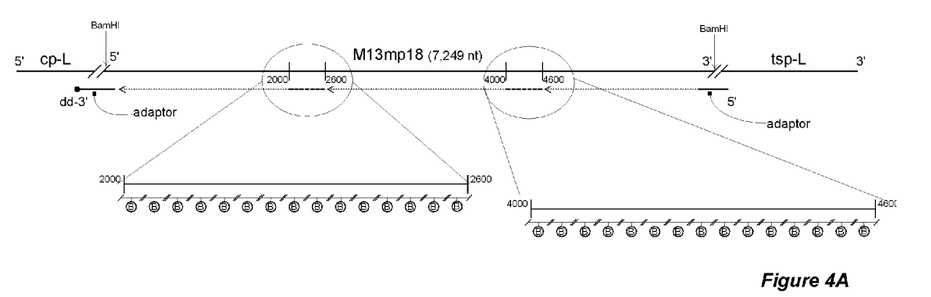
FIG. 4A shows a schematic representation of a Left barcode label L(11) with two "bulky" elements encoded in it.

The two bits that are encoded in each barcode label are contained in the 600 nucleotide regions between nucleotide 2000 and 2600 and between nucleotide 4000 and 4600 of M13mp18, as numbered from the site of BamHI digestion as shown in FIG. 4A. When any of these regions comprises a "bulky" element, as described below, it makes the value of the bit equal "1". When the region is comprised of regular double-stranded DNA, the bit value equals "0".

Figure 4B:
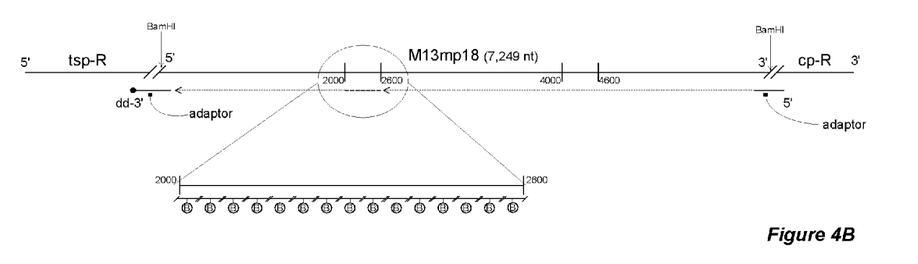
FIG. 4B shows a schematic representation of a Right barcode label R(10) with one "bulky" and one "slim" elements encoded in it.
Figure 4C:
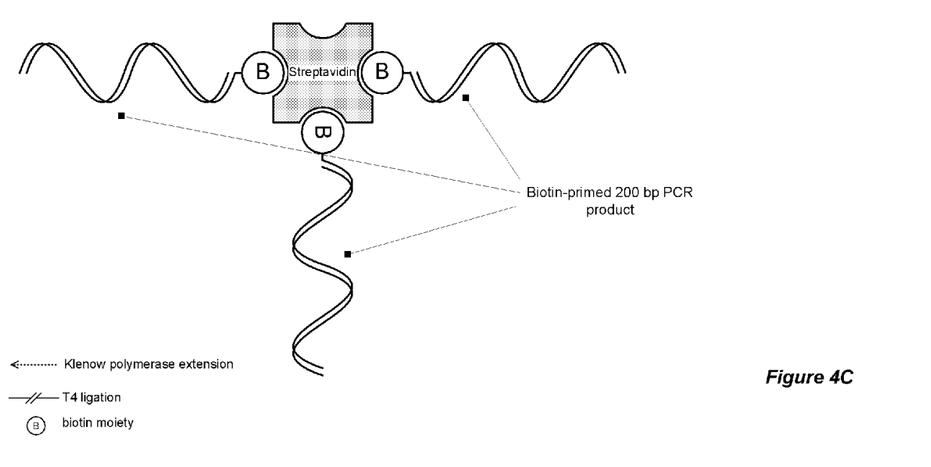
FIG. 4C shows a schematic representation of a "bulky" electroactive subelement based on streptavidin and DNA. Fifteen such subelements, each having a single unoccupied binding site for biotin, bind to the biotin moieties on the barcode labels shown in FIGS. 4A and 4B to form one electronically detectable "bulky" element.

To encode the bit-value of "1" (or in other words to designate the position of a "bulky" element) fifteen 40-mer oligonucleotides that are complimentary to the M13mp18 sequence in the corresponding region (2000-2600 or 4000-4600, or both), and modified with an internal biotin moiety in the middle of their sequence, are annealed to the linearized M13mp18 DNA for 30 minutes in 1×SSC as shown in FIGS. 4A and 4B. A 3× molar excess of the oligonucleotide over the M13mp18 DNA is used.

2. Ligation of Target-Specific Probes and Capture Probes to the NanoTape Termini Two oligonucleotide probes are ligated to the termini of each L and R barcode in a mirror-image configuration. For the L barcode label, a phosphorylated target specific probe "L" (tsp-L) is ligated to the 3' end, and a capture probe (cp-L) is ligated to the 5' end of a M13mp18 DNA (FIG. 4A). The sequence of tsp-L is complimentary to the 3' region targeted on the target molecule. The sequence of cp-L is complimentary to a capture sequence found on the surface of magnetic nanospheres (see below).

For the R barcode label, a target specific probe R (tsp-R), complimentary to the 5' target region of the target molecule, is ligated to the 5' end of a M13mp18 nanoTape (FIG. 4B). A phosphorylated capture probe R (cp-R), complimentary to a capture sequence found on the surface of a diamagnetic nanoparticle, is ligated to the 3' end of the right M13mp18 nanoTape.

Bridging adaptor oligonucleotides are used for the ligation of the terminal probes to the nanoTape termini. The adaptor oligonucleotide for the 5' terminal probes (cp-L and tsp-R) carry a dideoxy nucleotide at their 3' ends, which prevents extension by a DNA polymerase (FIGS. 4a and 4B). The single stranded regions of the nanoTape are converted to doublestranded by treatment with a Klenow polymerase and dNTPs. The nicks are ligated with T4 ligase. The dideoxy adaptors prevent conversion of cp-L and tsp-R into double-stranded duplexes.

There are four tsp-L and four tsp-R probes for each of the four nanoTapes, so that 16 pairs of Left-Right labels are synthesized.

3. Synthesis of "Bulky" Elements

The "bulky" elements, or the "1"s in this example are DNA-streptavidin complexes. Streptavidin is a protein that binds tightly to biotin. Four biotin moieties bind to a single streptavidin dimer. A 200 base-pair DNA fragment, with biotin at the 5' end of its "sense" strand, is synthesized via PCR using Lambda bacteriophage as a template and a biotinilated 5' primer.

The biotinilated DNA fragment is mixed with streptavidin in a 3.2:1 molar ratio and incubated for 1 hour at room temperature. The ratio is picked to stochastically favour creation of monovalent "bulky" complexes that have three DNA fragments per streptavidin and one available biotin binding site for attachment to the nanoTape (FIG. 4C). A small fraction of the resulting complexes contain four DNA fragments per streptavidin which will not attach to the nanoTape. The presence of polyvalent complexes (with two biotin binding sites or more) is undesirable as it could lead to attachment to multiple sites on the nanoTape or (rarely) to multiple nanoTapes.

While not intending to be bound by any particular mechanism, the "bulky" elements designed in this way can block the transport of redox mediators to the nanoelectrode, when in proximity to the nanoelectrode, via three possible mechanisms:

(i) Physical blockage. A set of 15 "bulky" elements that define one bit when attached to the corresponding sites on the nanoTape constitutes a stretch of dendrimeric DNA nanostructure about 200 nm long with 45 protruding DNA tentacles each of which is about 66 nm long. Such thick nanostructure presents a physical barrier for the diffusion of the redox compound to the nanoelectrode.

(ii) Entrhropic exclusion. Since the protruding DNA tentacles are not rigid they also exclude the mediator via enthropic exclusion.

(iii) Electrostatic repulsion. In this example the redox mediator is negatively charged and is being repelled by the negatively charged DNA nanostructure via electrostatic repulsion. The magnitude of this repulsion can be controlled by varying the ionic strength of the supporting electrolyte.

4. Superparamagnetic and Diamagnetic Nanospheres

Superparamagnetic nanoparticles are available from several vendors with various chemical functionalities on the surface that allow for modification with capture probes. In the present example, 250 nm, carboxylated, dextran-coated, superparamagnetic nanospheres, (available from G. Kisker CbR or other sources) are derivatized with an amino modified oligonucleotide using 1-ethyl-3-(3-dimethylaminopropyl) carbodiimide (EDC). The sequence of the oligonucleotide is the reverse compliment to that of cp-L (anti-cp-L).

Additionally, 200 nm carboxylated, diamagnetic, polysterene nanospheres (available from G. Kisker CbR or other sources) are derivatized with an amino modified oligonucleotide using EDC. The sequence of the oligonucleotide is the reverse compliment to that of cp-R (anti-cp-R).

The nanospheres are attached to the labels through the complementary DNA pairing of cp-L to anti-cp-L and cp-R to anti-cp-r.

B. Chip Containing Nanoelectrodes

Figure 5A:
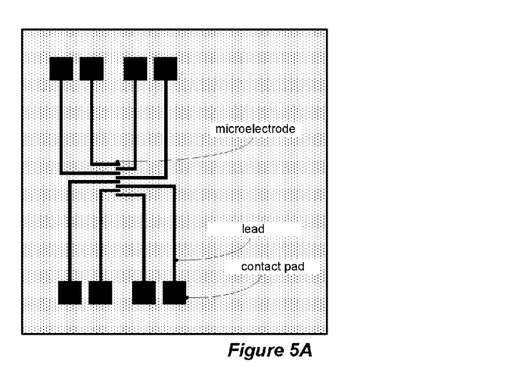
FIGS. 5A-D show a schematic representation of the steps involved in fabrication of a chip with eight nanoelectrodes and a microchannel. A. Gold microelectrodes on glass, top view. B. Insulating layer (silicon oxide), top view. C. Fabrication of nanoelectrodes, top and cross-sectional views. The area where the nanoelectrodes reside is magnified in the call-out circle (top view) and a cross-section along the dotted line pointed with an arrow is shown to the right. D. Fabrication of an open microchannel, top view (a cross-sectional view along the dotted line is shown to the right).

The nanoelectrode chip is fabricated by a combination of conventional photolithography and E-beam nanolithography. A 1"×1" glass coverslip is coated with a thin film of gold using chromium as a binding layer. Eight microelectrodes are etched out using conventional photolithography (FIGS. 5A and 5C, right panel). The electrode leads terminate in contact pads at the edge of the chip (FIG. 5A).

Figure 5B:
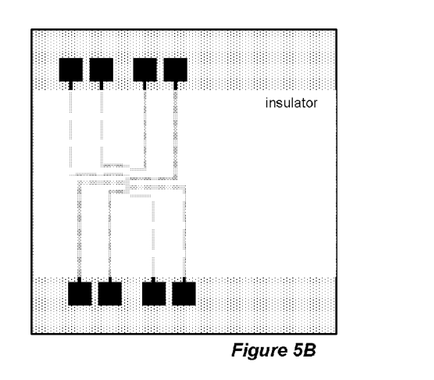
Figure 5C:
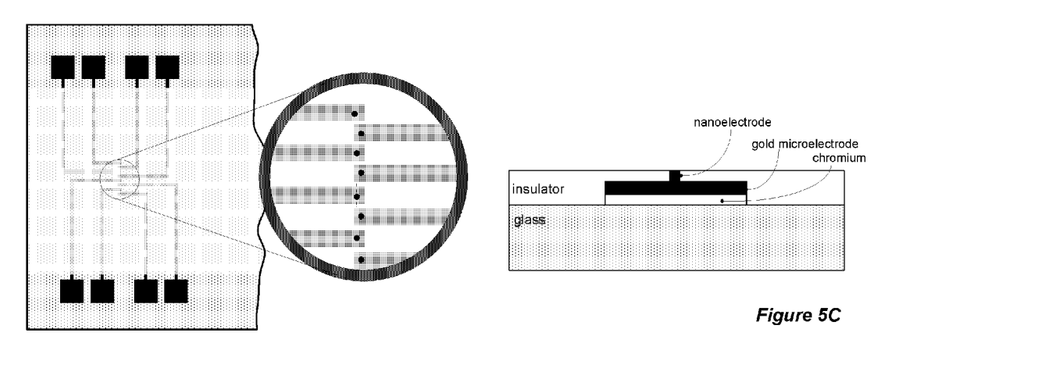

A 100 nm insulating layer of silicon oxide is deposited on top of the chip, with the exception of the contact pads, which are protected by photoresis (FIG. 5B). Holes with a diameter of 50 nm are etched in the insulating oxide layer, using E-beam nanolithography and PMMA photoresist, to expose the underlying gold layer of the microelectrodes. The holes are filled-in with gold by an evaporation and liftoff process that resembles fabrication of interconnecting vias in semiconductor chips (FIG. 5C, left panel). The surface is then planarized and polished.

Figure 5D:
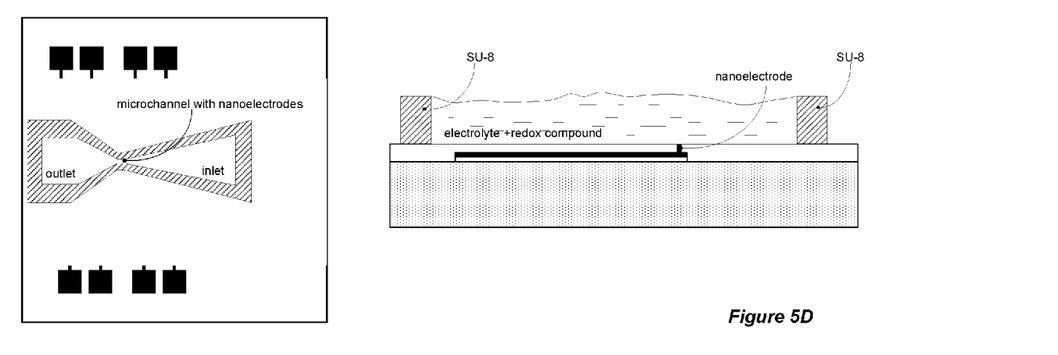

An open chamber is fabricated using SU-8 lithography to contain the electrolyte and the barcode labels as shown in FIG. 5D. The chamber has two compartments (inlet and outlet), separated by a microchannel that contains the nanoelectrodes. In this example the nanoelectrodes are the anodes and the counterelectrode is a grounded platinum wire in the outlet chamber.

C. Redox Mediator and Electrolyte

Ferrocene carboxylic acid (FcA) is used as the redox mediator. In addition to its benefits as a proven and suitable electrochemical redox probe (Cass, Davis et al. 1984) it offers an additional advantage in this particular implementation since its reduced form carries a negative charge, while the oxidized form is a neutral zwitterion.

The redox reaction at the anode is:

$$FcA^- \rightarrow Fc^+A^- + e^-$$

When the nanoTape is in the proximity of the nanoelectrode its negatively charged "bulky" elements exert electrostatic repulsive force on the reduced FcA, thus reducing its mass flow to the nanoelectrode and hence the current. Such electrostatic force does not act on the neutral oxidation product.

D. Procedure for Binding Barcode Labels to Individual mRNA Target Molecules

The 16 Left and 16 Right barcode labels are mixed in an approximately 1000× fold excess over the expected concentration of the most abundant target mRNA in 1 ml of 5×SSPE buffer and incubated for 16 hours at 60° C. in a microtube. A suspension containing the paramagnetic and diamagnetic beads in 3× excess over the total amount of barcode labels is added and the mixture is incubated for an additional 3 hours. At that point the electroactive elements described in Section A, subsection 3 of the present example are added to the mixture in 4× fold excess over total amount of barcode labels, and incubated for an additional 30 minutes. It is important to perform the binding of the beads to the barcodes before the elements are added to the reaction mixture to avoid any steric hindrance by the dendrimeric structures.

The magnetic spheres are pulled to the bottom of the tube with a magnet and washed three times with 0.1×SSPE. After the third wash the beads are pulled down and resuspended in 1.5 ml of 100 mM KCl and 10 mM FcA (reduced form).

E. Detection of Barcode Labels

Figure 6:
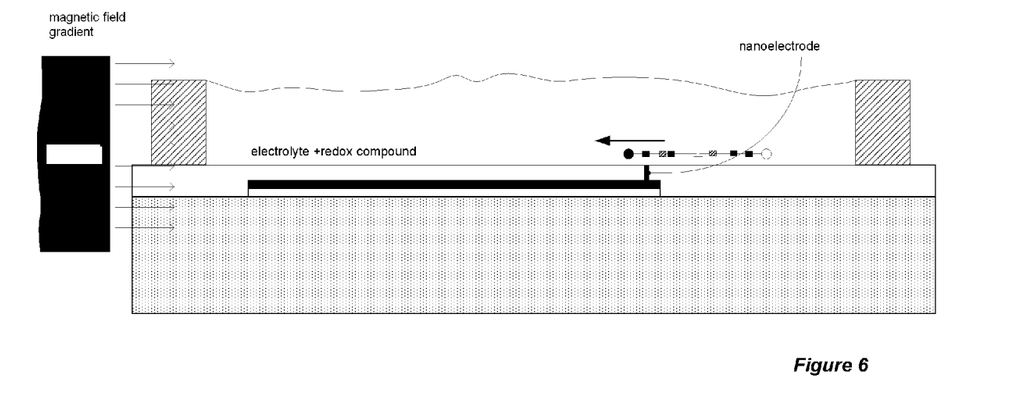
FIG. 6 shows a schematic representation of a magnetically tagged, dual barcode label streaming by a nanoelectrode in a microchannel containing electrolyte and a redox compound.

A 1 μl aliquot of the resuspended barcode labels from the previous paragraph is added to the inlet chamber of the chip which has been prefilled with buffer containing 100 mM KCl and 10 mM FcA (reduced form). The barcode labels and paramagnetic spheres are allowed to settle on the surface of the chip. A magnetic force is then applied from the outlet channel side of the chip that is parallel to its surface. Since the magnetic susceptibility of the paramagnetic nanosphere is higher than that of the media, which is in turn higher than the magnetic susceptibility of the diamagnetic nanosphere, the magnetic force is attractive on the paramagnetic end of the barcode label and repulsive on the diamagnetic end, respectively. This causes the barcode label to stretch and to move in the direction of the magnetic gradient. The movement is considerably slower than that of the free paramagnetic nanospheres, as well as nanospheres containing only the Left barcode label that are not bound to a target molecule and a Right label, which pass through the nanoelectrode channel first (FIG. 6).

Detection is accomplished by reading the current going through each nanoelectrode in the channel, from the contact pads, using a low-noise high-bandwidth amplifier/galvanometer.

As the dual barcode labels pass through the channel, they interfere with the mass transport of mediator to the surface of the nanoelectrodes and hence the current flowing through them. In the present example, for the L(11)R(01) barcode, an initial drop in the current is caused by the paramagnetic particle. This is followed by the two "1" bits on the Left barcode that each create a corresponding drop in the current, followed by a longer interval of high current that indicates the presence of a "0" bit on the Right barcode and then another dip for the "1" bit of the Right barcode followed by a large dip for the trailing diamagnetic sphere.

It will be understood that the instant invention is not limited to the particular formulations, process steps, and materials disclosed herein as such formulations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

All publications and patents mentioned herein are incorporated herein by reference for the purpose of describing and disclosing, for example, the constructs and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

REFERENCES

Arrigan, D. W. M. (2004). "Nanoelectrodes, nanoelectrode arrays and their applications." Analyst 129(12): 1157-1165.

Cass, A. E. G., G. Davis, et al. (1984). "Ferrocene-Mediated Enzyme Electrode for Amperometric Determination of Glucose." Analytical Chemistry 56(4):667-671.

Ciszkowska, M., Z. Stojek, et al. (1995). "Voltammetric Reduction of Polyprotic Acids at the Platinum Microelectrode-Dependence on Supporting Electrolyte." Journal of Electroanalytical Chemistry 398(1-2): 49-56.

Current Protocols in Molecular Biology (ed. Ausubel et al., Greene Publ., New York 1989

Demidov, V. V. (2003). "PNA and LNA throw light on DNA." Trends Biotechnol 21(1): 4-7.

Dimitrov, K. (2001). Methods for Detection and Quantification of Analytes in Complex Mixtures.

Esplandiu, M. J., V. G. Bittner, et al. (2004). "Nanoelectrode scanning probes from fluorocarbon-coated single-walled carbon nanotubes." Nano Letters 4(10): 1873-1879.

Garcia, R., R. V. Martinez, et al. (2006). "Nano-chemistry and scanning probe nanolithographies." Chemical Society Reviews 35(1): 29-38.

Gates, B. D., Q. B. Xu, et al. (2004). "Unconventional nanofabrication." Annual Review of Materials Research 34: 339-372.

Hafner, J. H., C. L. Cheung, et al. (2001). "High-yield assembly of individual single-walled carbon nanotube tips for scanning probe microscopies." Journal of Physical Chemistry B 105(4): 743-746.

Hames and Higgins. Nucleic Acids research Hybridization: A Practical Approach, IRL Press, Oxford (1991)

Ishijima, A. and T. Yanagida (2001). "Single molecule nanobioscience." Trends Biochem Sci 26(7): 438-44.

Koehne, J., J. Li, et al. (2004). "The fabrication and electrochemical characterization of carbon nanotube nanoelectrode arrays." Journal of Materials Chemistry 14(4): 676-684.

Koehne, J., J. Li, et al. (2003). "Carbon nanotube nanoelectrode array for ultrasensitive DNA detection." Abstracts of Papers of the American Chemical Society 226: U119-U120.

Mannion, J. T., C. H. Reccius, et al. (2006). "Conformational analysis of single DNA molecules undergoing entropically induced motion in nanochannels." Biophys J 90(12): 4538-45.

Matsuura, S., H. Kurita, et al. (2002). "One-end immobilization of individual DNA molecules on a functional hydrophobic glass surface." J Biomol Struct Dyn 20(3): 429-36.

Michalet, X., R. Ekong, et al. (1997). "Dynamic molecular combing: stretching the whole human genome for high-resolution studies." Science 277(5331): 1518-23.

Onclin, S., B. J. Ravoo, et al. (2005). "Engineering silicon oxide surfaces using self-assembled monolayers." Angewandte Chemie-International Edition 44(39): 6282-6304.

Orum, H. and J. Wengel (2001). "Locked nucleic acids: a promising molecular family for gene-function analysis and antisense drug development." Curr Opin Mol Ther 3(3): 239-43.

Rooney, M. B., D. C. Coomber, et al. (2000). "Achievement of near-reversible behavior for the [Fe(CN)(6)](3-/4-) redox couple using cyclic voltammetry at glassy carbon, gold, and platinum macrodisk electrodes in the absence of added supporting electrolyte." Analytical Chemistry 72(15): 3486-3491.

Schena, M. (2003). Microarray analysis. Hoboken, N.J., Wiley-Liss.

Stevens, N. P. C., M. B. Rooney, et al. (2001). "A comparison of simulated and experimental voltammograms obtained for the [Fe(CN)(6)](3-/4-) couple in the absence of added supporting electrolyte at a rotating disk electrode." Journal of Physical Chemistry A 105(40): 9085-9093.

Stoltenburg, R., C. Reinemann, et al. (2005). "FluMag-SELEX as an advantageous method for DNA aptamer selection." Analytical and Bioanalytical Chemistry 383(1): 83-91.

Strick, T., J. Allemand, et al. (2000). "Twisting and stretching single DNA molecules." Prog Biophys Mol Biol 74(1-2): 115-40.

Tijssen, P. (1993). Hybridization with nucleic acid probes. Amsterdam; New York, Elsevier.

Tseng, A. A., A. Notargiacomo, et al. (2005). "Nanofabrication by scanning probe microscope lithography: A review." Journal of Vacuum Science & Technology B 23(3): 877-894.

Watanabe, M. (2005). Method of Forming a Resist Pattern and Fabricating Tapered Features. US.

Watarai, H., M. Suwa, et al. (2004). "Magnetophoresis and electromagnetophoresis of microparticles in liquids." Analytical and Bioanalytical Chemistry 378(7): 1693-1699.

The embodiments of the invention in which an exclusive property of privilege is claimed are defined as follows:

1. A method for the detection of individual target analyte molecules in a sample comprising:
   (a) contacting one or more labels, each of which comprises a target specific probe capable of binding the target analyte molecule attached to a polymeric molecule or filament which comprises one or more elements with different electrical properties as detected by a nanoelectrode, with a target analyte molecule;
   (b) moving label which comprises the target specific probe that is bound to the target analyte molecule sufficiently close to a nanoelectrode such that the electric current of the nanoelectrode is changed; and
   (c) detecting the changes in electric current produced in the nanoelectrode by the elements with different electrical properties in label that is bound to the target analyte molecule, wherein the method does not include detecting changes in fluorescence.

2. The method according to claim 1 wherein the label that is bound to the target analyte molecule is moved using optical tweezers, AC electric fields, hydrodynamic forces or fluidic forces.

3. The method according to claim 1 wherein the label that is bound to the target analyte molecule is moved using magnetic forces.

4. The method according to claim 1 wherein the changes in electric current produced in the nanoelectrode by the elements with different electrical properties in label that is bound to the target analyte molecule are detected using a galvanometer with an electronic amplifier.

5. The method according to claim 1 wherein the target specific probe is a nucleic acid molecule complementary to the target analyte molecule and the polymeric molecule is a nucleic acid molecule.

6. The method according to claim 1 comprising two or more labels wherein the target specific probe of each label is different from each of the other labels.

7. The method according to claim 1 wherein the polymeric molecule or filament comprises two elements with different electrical properties as detected by a nanoelectrode.

8. The method according to claim 1 wherein the label further comprises one or more additional elements capable of providing sufficient stretching of the label to allow each of the elements with different electrical properties to be separately detected.

9. The method according to claim 8 having one additional element comprising a magnetic nanosphere.

10. The method according to claim 8 having a first additional element comprising a magnetic nanosphere and a second additional element comprising a hydrophobic moiety.

11. The method according to claim 1 wherein the nanoelectrode has a critical dimension of about 20 nm to about 100 nm.

12. The method according to claim 1 wherein the nanoelectrode has a critical dimension of less than about 100 nm.

13. The method according to claim 1 wherein the nanoelectrode is fabricated from gold, platinum or carbon nanotubes.

14. The method according to claim 1 further comprising one or more additional nanoelectrodes fabricated to form an array.

15. The method according to claim 1 wherein the nanoelectrode is located at the bottom of a channel in a silicon, glass or plastic chip.

16. The method according to claim 15 wherein the chip contains one or more electronic components capable of amplifying the changes in electric current produced in the nanoelectrode.

17. The method according to claim 16 wherein the one or more electronic components comprise a field-effect transistor.

18. The method according to claim 17 wherein the field-effect transistor is a metal-oxide-semiconductor field-effect transistor.

* * * * *